US010358655B1

(12) United States Patent
Sundquist et al.

(10) Patent No.: US 10,358,655 B1
(45) Date of Patent: Jul. 23, 2019

(54) ATTENUATED PROTEIN EXPRESSION VECTORS AND ASSOCIATED METHODS

(71) Applicant: University of Utah Research Foundation, Salt Lake City, UT (US)

(72) Inventors: Wesley I. Sundquist, Salt Lake City, UT (US); Eiji Morita, Osaka (JP); Jun Arii, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/414,479

(22) Filed: Jan. 24, 2017

Related U.S. Application Data

(63) Continuation of application No. 13/963,938, filed on Aug. 9, 2013, now abandoned, which is a continuation-in-part of application No. 13/929,657, filed on Jun. 27, 2013, now abandoned.

(60) Provisional application No. 61/690,459, filed on Jun. 27, 2012.

(51) Int. Cl.
| | | |
|---|---|---|
| C12N 15/85 | (2006.01) | |
| C12N 7/00 | (2006.01) | |
| C12N 15/113 | (2010.01) | |
| C12Q 1/6876 | (2018.01) | |

(52) U.S. Cl.
CPC ............... *C12N 15/85* (2013.01); *C12N 7/00* (2013.01); *C12N 15/113* (2013.01); *C12Q 1/6876* (2013.01); *C12N 2310/14* (2013.01); *C12N 2710/16143* (2013.01); *C12N 2830/60* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 5,487,993 A | 1/1996 | Herrnstadt et al. |
| 5,766,891 A | 6/1998 | Shuman |
| 5,827,657 A | 10/1998 | Herrnstadt et al. |
| 5,851,808 A | 12/1998 | Elledge et al. |
| 5,888,732 A | 3/1999 | Hartley et al. |
| 5,910,438 A | 6/1999 | Bernard et al. |
| 6,143,557 A | 11/2000 | Hartley et al. |
| 6,171,861 B1 | 1/2001 | Hartley et al. |
| 6,180,407 B1 | 1/2001 | Bernard et al. |
| 6,270,969 B1 | 8/2001 | Hartley et al. |

OTHER PUBLICATIONS

Blast; Alignment Of Seq Id No. 1. Dated Oct. 29, 2015; http://blast.ncbi.nlm.nih.gov/Blast.cgi#alnHdr_92918407.
Cullen; Enhancing and confirming the specificity of RNAi experiments; Nature Methods; Aug. 2006; pp. 677-681; vol. 3; Nature Publishing Group.
Dordor et al.; Essential and supporting host cell factors for HIV-1 budding; Future Microbiology; Oct. 2011; pp. 1159-1170; vol. 6, No. 10.
Elbashir et al.; Duplexes of 21-nucleotide RNAs mediate RNA interference in cultured mammalian cells; Nature; May 2001; pp. 494-498; vol. 411; MacMillan Magazines Ltd.
Falschlehner et al.; High throughput RNAi screening to dissect cellular pathways: a show-to guide; Biotechnol. J.; 2010; pp. 368-376; vol. 5.
Garrus et al.; Tsg 101 and the vacuolar protein sorting pathway are essential for HIV-1 budding; Cell; Oct. 5, 2001; pp. 55-65; vol. 107; Cell Press.
Heinemeyer et al.; Databases on transcriptional regulation: TRANSFAC, TRRD and COMPEL; Nucleic Acids Research; 1998; pp. 362-367; vol. 26, No. 1; Oxford University Press.
Henne et al.; The ESCRT Pathway; Developmental Cell; Jul. 19, 2011; pp. 77-91; vol. 21; Elsevier Inc.
Houzet et al.; Genome-wide screening using RNA interference to study host factors in viral replication and pathogenesis; Exp. Biol. Med. (Maywood); Aug. 1, 2011; pp. 962-967; vol. 236.
Howard et al.; CHMP1 functions as a member of a newly defined family of vesicle trafficking proteins; Journal of Cell Science; 2001; pp. 2395-2404; vol. 114; The Company of Biologists Ltd.
Hurley et al.; Membrane budding and scission by the ESCRT machinery: it's all in the neck; Nature Review Molecular Cell Biology; Aug. 2010; 24 pages; vol. 11, No. 8.
Lassus et al.; Confirming specificity of RNAi in mammalian cells; Sci. STKE; Aug. 2002; page 13.
Ma et al.; Gene down-regulation with short hairpin RNAs and validation of specificity by inducible rescue in mammalian cells; Current Protocols in Cell Biology; Dec. 2010; Chapter 27, Unit 27.2; John Wiley and Sons.
Martin et al.; Applications of RNA interference in mammalian systems; Annu.Rev. Genomics Hum. Genet.; 2007; pp. 81-108; vol. 8.
Martin-Serrano et al.; Divergent retroviral late-budding domains recruit vacuolar protein sorting factors by using alternative adaptor proteins; Proceedings of the National Academy of Sciences of the United States of America; Oct. 2003; pp. 12414-12419; vol. 100, No. 21; PNAS.
Martin-Serrano et al.; Host factors involved in retroviral budding and release; Nature Reviews Microbiology; Jul. 2011; pp. 519-531; vol. 9; MacMillan Publishers Limited.

(Continued)

*Primary Examiner* — Mindy G Brown
(74) *Attorney, Agent, or Firm* — Thorpe North & Western, LLP; David W. Osborne

(57) ABSTRACT

A non-natural modified CMV promoter is provided. Such a promoter can include a promoter nucleotide sequence that is at least 80% homologous to a sequence selected from the group consisting of SEQ ID 01, SEQ ID 02, SEQ ID 03, SEQ ID 04, SEQ ID 05, SEQ ID 06, SEQ ID 07, and compliments thereof.

16 Claims, 4 Drawing Sheets

Specification includes a Sequence Listing.

(56) References Cited

OTHER PUBLICATIONS

Morita et al.; ESCRT-III Protein Requirements for HIV-1 Budding; Cell Host & Microbe; Mar. 17, 2011; pp. 235-242; vol. 9; Elsevier Inc.

Morita et al.; Human ESCRT-III and VPS4 proteins are required for centrosome and spindle maintenance; Proceedings of the National Academy of Science of the United States of America; Jul. 20, 2010; pp. 12889-12894; PNAS.

Naldini et al.; Efficient transfer, integration, and sustained long-term expression of the transgene in adult rat brains injected with a lentiviral vector; Proceedings of the National Academy of Science of the United States of America; Oct. 1996; pp. 11382-11388; National Academy of Sciences.

Pache et al.; Indentifying HIV-1 host cell factors by genome-scale RNAi screening; Jan. 2011; pp. 3-12; vol. 53, Issue 1.

Sakurai et al; Silencing of gene expression in cultured cells using small interfering RNAs; Current Protocols in Cell Biology, Chapter 27; Jun. 2010; pp. 21-28; Unit 27; John Wiley and Sons, Inc.

Schug; Using TESS to predict transcription factor binding sites in DNA sequence; In Baxivanis (Ed.) Current Protocols in Bioinformatics 2009; Chapter 2, Unit 2.6; John Wiley & Sons, Ltd.

Sigoillot et al.; Vigilance and validation: Keys to success in RNAi screening; ACS Chem. Biol.; Jan. 21, 2011; pp. 47-60; vol. 6.

Stinski et al.; Role of the cytomegalovirus major immediate early enhancer in acute infection and reactivation from latency; Med. Microbiol Immunol; 2008; pp. 223-231; vol. 197; Springer.

Storvold et al,; A Retroviral Vector For siRNA Expression In Mammalian Cells; Institute of Medical Genetics, University of Oslo, Norway; Mar. 2006 See Appendix B For Complete Sequence Of ShRNA expression Vector pSiRPG. Accessed Oct. 29, 2015. https://www.ncbi.nlm.nih.gov/nucleotide/92918407?report=genbank&log$=nuclanlign&blast_rank=1&RID=34Y9XW9C015.

Strack et al.; AIP1/ALIX is a Binding Partner for HIV-1 p6 and E1AV p9 Functioning in Virus Budding; Cell; Sep. 19, 2003; pp. 689-699; vol. 114; Cell Press.

Von Scwhedler et al.; The Protein network of HIV-1 budding; Cell; Sep. 19, 2003; pp. 701-713; vol. 114; Cell Press.

Zamborlini et al.; Release of autoinhibition converts ESCRT-111 components into potent inhibitors of HIV-1 budding; Proceedings of the National Academy of Sciences of the United States of America; Dec. 12, 2006; pp. 19140-19145; vol. 103, No. 50; PNAS.

U.S. Appl. No. 13/929,657, filed Jun. 27, 2013; Wesley I. Sundquist.

SEQUENCE LISTING

<160> NUMBER OF SEQ ID NOS: 13

<210> SEQ ID NO 1
<211> LENGTH: 673
<212> TYPE: DNA
<213> ORGANISM: Homo sapiens

<400> SEQUENCE: 1

```
cgctgagtag tgcgcgagca aaatttaagc tacaacaagg caaggcttga ccgacaattg    60
catgaagaat ctgcttaggg ttaggcgttt tgcgctgctt cgcgatgtac gggccagata   120
tacgcgtcat gacccttatgg gactttccta cttggcagta catctacgta ttagtcatcg   180
ctattaccat ggtgatgcgg ttttggcagt acatcaatgg gcgtggatag cggtttgact   240
cacggggatt tccaagtctc cacccattg acgtcaatgg gagtttgttt tggcaccaaa   300
atcaacggga cttttccaaaa tgtcgtaaca actccgcccc attgacgcaa atgggcggta   360
ggcgtgtacg gtgggaggtc tatataagca gagctctctg gctaactaga gaacccactg   420
cttactggct tatcgaaatt aatacgactc actataggga gacccaagct ggctagcgtt   480
taaacgggcc ctctagaatt atcgatccgg aggtacccgg gcggccgcga gtcttcgaat   540
tcaaacgcgt ctcgagaagc ttgctagcag atcttttttcc ctctgccaaa aattatgggg   600
acatcatgaa gcccctttgag cacttaagtt taaaccgctg atcagcctcg actgtgcctt   660
ctagttgcca gcc                                                       673
```

<210> SEQ ID NO 2
<211> LENGTH: 573
<212> TYPE: DNA
<213> ORGANISM: Homo sapiens

<400> SEQUENCE: 2

```
cgctgagtag tgcgcgagca aaatttaagc tacaacaagg caaggcttga ccgacaattg    60
catgaagaat ctgcttaggg ttaggcgttt tgcgctgctt cgcgatgtac gggccagata   120
tacgcgttag cggtttgact cacggggatt tccaagtctc cacccattg acgtcaatgg   180
gagtttgttt tggcaccaaa atcaacggga cttttccaaaa tgtcgtaaca actccgcccc   240
attgacgcaa atgggcggta ggcgtgtacg gtgggaggtc tatataagca gagctctctg   300
gctaactaga gaacccactg cttactggct tatcgaaatt aatacgactc actataggga   360
gacccaagct ggctagcgtt taaacgggcc ctctagaatt atcgatccgg aggtacccgg   420
gcggccgcga gtcttcgaat tcaaacgcgt ctcgagaagc ttgctagcag atcttttttcc   480
ctctgccaaa aattatgggg acatcatgaa gcccctttgag cacttaagtt taaaccgctg   540
atcagcctcg actgtgcctt ctagttgcca gcc                                 573
```

<210> SEQ ID NO 3
<211> LENGTH: 539
<212> TYPE: DNA
<213> ORGANISM: Homo sapiens

<400> SEQUENCE: 3

```
cgctgagtag tgcgcgagca aaatttaagc tacaacaagg caaggcttga ccgacaattg    60
catgaagaat ctgcttaggg ttaggcgttt tgcgctgctt cgcgatgtac gggccagata   120
tacgcgtacc ccattgacgt caatgggagt tgttttggc accaaaatca cgggactttt   180
ccaaaatgtc gtaacaactc cgccccattg acgcaaatgg gcggtaggcg tgtacggtgg   240
gaggtctata taagcagagc tctctggcta actagagaac ccactgctta ctggcttatc   300
gaaattaata cgactcacta tagggagacc caagctggct agcgtttaaa cgggccctct   360
agaattatcg atccggaggt acccggcggg ccgcgagtct cgaattcaa acgcgtctcg   420
agaagcttgc tagcagatct ttttccctct gccaaaaatt atggggacat catgaagccc   480
```
cttgagcact taagtttaaa ccgctgatca gcctcgactg tgccttctag ttgccagcc         539

<210> SEQ ID NO 4
<211> LENGTH: 500
<212> TYPE: DNA
<213> ORGANISM: Homo sapiens

<400> SEQUENCE: 4
cgctgagtag tgcgcgagca aaatttaagc tacaacaagg caaggcttga ccgacaattg          60
catgaagaat ctgcttaggg ttaggcgttt tgcgctgctt cgcgatgtac gggccagata         120
tacgcgtatc aacgggactt tccaaaatgt cgtaacaact ccgccccatt gacgcaaatg         180
ggcggtaggc gtgtacggtg ggaggtctat ataagcagag ctctctggct aactagagaa         240
cccactgctt actggcttat cgaaattaat acgactcact atagggagac ccaagctggc         300
tagcgtttaa acgggccctc tagaattatc gatccggagg tacccgggcg gccgcgagtc         360
ttcgaattca aacgcgtctc gagaagcttg ctagcagatc ttttcccctc tgccaaaaat         420
tatggggaca tcatgaagcc ccttgagcac ttaagtttaa accgctgatc agcctcgact         480
gtgccttcta gttgccagcc                                                    500

<210> SEQ ID NO 5
<211> LENGTH: 480
<212> TYPE: DNA
<213> ORGANISM: Homo sapiens

<400> SEQUENCE: 5
cgctgagtag tgcgcgagca aaatttaagc tacaacaagg caaggcttga ccgacaattg          60
catgaagaat ctgcttaggg ttaggcgttt tgcgctgctt cgcgatgtac gggccagata         120
tacgcgttgt cgtaacaact ccgccccatt gacgcaaatg ggcggtaggc gtgtacggtg         180
ggaggtctat ataagcagag ctctctggct aactagagaa cccactgctt actggcttat         240
cgaaattaat acgactcact atagggagac ccaagctggc tagcgtttaa acgggccctc         300
tagaattatc gatccggagg tacccgggcg gccgcgagtc ttcgaattca aacgcgtctc         360
gagaagcttg ctagcagatc ttttcccctc tgccaaaaat tatggggaca tcatgaagcc         420
ccttgagcac ttaagtttaa accgctgatc agcctcgact gtgccttcta gttgccagcc         480

<210> SEQ ID NO 6
<211> LENGTH: 460
<212> TYPE: DNA
<213> ORGANISM: Homo sapiens

<400> SEQUENCE: 6
cgctgagtag tgcgcgagca aaatttaagc tacaacaagg caaggcttga ccgacaattg          60
catgaagaat ctgcttaggg ttaggcgttt tgcgctgctt cgcgatgtac gggccagata         120
tacgcgtatt gacgcaaatg ggcggtaggc gtgtacggtg ggaggtctat ataagcagag         180
ctctctggct aactagagaa cccactgctt actggcttat cgaaattaat acgactcact         240
atagggagac ccaagctggc tagcgtttaa acgggccctc tagaattatc gatccggagg         300
tacccgggcg gccgcgagtc ttcgaattca aacgcgtctc gagaagcttg ctagcagatc         360
ttttcccctc tgccaaaaat tatggggaca tcatgaagcc ccttgagcac ttaagtttaa         420
accgctgatc agcctcgact gtgccttcta gttgccagcc                              460

<210> SEQ ID NO 7
<211> LENGTH: 309

```
<212> TYPE: DNA
<213> ORGANISM: Homo sapiens

<400> SEQUENCE: 7
cgctgagtag tgcgcgagca aaatttaagc tacaacaagg caaggcttga ccgacaattg      60
catgaagaat ctgcttaggg ttaggcgttt tgcgctgctt cgcgatgtac gggccagata     120
tacgcgttct agaattatcg atccggaggt acccgggcgg ccgcgagtct tcgaattcaa     180
acgcgtctcg agaagcttgc tagcagatct ttttccctct gccaaaaatt atggggacat     240
catgaagccc cttgagcact taagtttaaa ccgctgatca gcctcgactg tgccttctag     300
ttgccagcc                                                             309

<210> SEQ ID NO 8
<211> LENGTH: 990
<212> TYPE: DNA
<213> ORGANISM: Homo sapiens

<400> SEQUENCE: 8
cgctgagtag tgcgcgagca aaatttaagc tacaacaagg caaggcttga ccgacaattg      60
catgaagaat ctgcttaggg ttaggcgttt tgcgctgctt cgcgatgtac gggccagata     120
tacgcgttga cattgattat tgactagtta ttaatagtaa tcaattacgg ggtcattagt     180
tcatagccca tatatggagt tccgcgttac ataacttacg gtaaatggcc cgcctggctg     240
accgcccaac gacccccgcc cattgacgtc aataatgacg tatgttccca tagtaacgcc     300
aatagggact ttccattgac gtcaatgggt ggagtattta cggtaaactg cccacttggc     360
agtacatcaa gtgtatcata tgccaagtac gccccctatt gacgtcaatg acggtaaatg     420
gcccgcctgg cattatgccc agtacatgac cttatgggac tttcctactt ggcagtacat     480
ctacgtatta gtcatcgcta ttaccatggt gatgcggttt tggcagtaca tcaatgggcg     540
tggatagcgg tttgactcac ggggatttcc aagtctccac cccattgacg tcaatgggag     600
tttgttttgg caccaaaatc aacgggactt tccaaaatgt cgtaacaact ccgccccatt     660
gacgcaaatg ggcggtaggc gtgtacggtg ggaggtctat ataagcagag ctctctggct     720
aactagagaa cccactgctt actggcttat cgaaattaat acgactcact ataggagac     780
ccaagctggc tagcgtttaa acgggccctc tagaattatc gatccggagg tacccgggcg     840
gccgcgagtc ttcgaattca aacgcgtctc gagaagcttg ctagcagatc tttttccctc     900
tgccaaaaat tatggggaca tcatgaagcc ccttgagcac ttaagtttaa accgctgatc     960
agcctcgact gtgccttcta gttgccagcc                                     990

<210> SEQ ID NO 9
<211> LENGTH: 19
<212> TYPE: RNA
<213> ORGANISM: Homo sapiens

<400> SEQUENCE: 9
cguacgcgga auacuucga                                                   19

<210> SEQ ID NO 10
<211> LENGTH: 19
<212> TYPE: RNA
<213> ORGANISM: Homo sapiens

<400> SEQUENCE: 10
aggcagagau cauggauau                                                   19
```

```
<210> SEQ ID NO 11
<211> LENGTH: 19
<212> TYPE: RNA
<213> ORGANISM: Homo sapiens

<400> SEQUENCE: 11
ggaacagaau cgagaguua                                                  19

<210> SEQ ID NO 12
<211> LENGTH: 19
<212> TYPE: DNA
<213> ORGANISM: Homo sapiens

<400> SEQUENCE: 12
aggcagagat catggatat                                                  19

<210> SEQ ID NO 13
<211> LENGTH: 19
<212> TYPE: DNA
<213> ORGANISM: Homo sapiens

<400> SEQUENCE: 13
aagctgaaat tatggatat                                                  19
```

ATTENUATED PROTEIN EXPRESSION VECTORS AND ASSOCIATED METHODS

PRIORITY DATA

This application is a continuation of U.S. patent application Ser. No. 13/963,938, filed Aug. 9, 2013, which is a continuation-in-part of U.S. patent application Ser. No. 13/929,657, filed on Jun. 27, 2013, which claims the benefit of U.S. Provisional Patent Application Ser. No. 61/690,459, filed on Jun. 27, 2012, both of which are incorporated herein by reference.

GOVERNMENT INTEREST

This invention was made with government support under Grant Number AI051174 awarded by the National Institutes of Health. The government has certain rights in the invention.

BACKGROUND OF THE INVENTION

Small interfering RNAs (siRNAs) are commonly employed, both individually and on a genome-wide scale, to degrade specific mRNAs and thus allow testing of the cellular functionality for the proteins encoded by the mRNA. siRNA depletion experiments can be extended further using "rescue" procedures in which the target protein is re-expressed from a transiently transfected vector that encodes an altered mRNA that is resistant to siRNA silencing. Such rescue experiments can be useful for confirming siRNA specificity because the exogenously expressed protein should rescue the loss-of-function phenotype. The experiment can also enable genetic analysis in cultured cells because the functional effects of specific mutations can be tested.

Phenotypic rescue experiments can fail, however, when the rescuing protein is expressed at, for example, such a high level that it dominantly inhibits the pathway of interest. This problem can often be alleviated by reducing the quantity of transfected expression vector, but this approach can fail if the overall transfection efficiency is reduced.

SUMMARY OF THE INVENTION

In one aspect, a non-natural modified CMV promoter is provided having a promoter nucleotide sequence that is at least 80% homologous to a sequence selected from SEQ ID NO: 01, SEQ ID NO: 02, SEQ ID NO: 03, SEQ ID NO: 04, SEQ ID NO: 05, SEQ ID NO: 06, SEQ ID NO: 07, and compliments thereof. In another aspect, the promoter can have the promoter nucleotide sequence selected from SEQ ID NO: 01, SEQ ID NO: 02, SEQ ID NO: 03, SEQ ID NO: 04, SEQ ID NO: 05, SEQ ID NO: 06, SEQ ID NO: 07, or compliments thereof. In yet another aspect, the promoter can have the promoter nucleotide sequence of SEQ ID NO: 01 or a compliment thereof. In yet another aspect, the promoter can have the promoter nucleotide sequence of SEQ ID NO: 02 or a compliment thereof. In yet another aspect, the promoter can have the promoter nucleotide sequence of SEQ ID NO: 03 or a compliment thereof. In yet another aspect, the promoter can have the promoter nucleotide sequence of SEQ ID NO: 04 or a compliment thereof. In yet another aspect, the promoter can have the promoter nucleotide sequence of SEQ ID NO: 05 or a compliment thereof. In yet another aspect, the promoter can have the promoter nucleotide sequence of SEQ ID NO: 06 or a compliment thereof. In yet another aspect, the promoter can have the promoter nucleotide sequence of SEQ ID NO: 07 or a compliment thereof.

In yet another aspect, an expression vector is provided including a non-natural modified CMV promoter having a promoter nucleotide sequence that is at least 80% homologous to a sequence selected from SEQ ID NO: 01, SEQ ID NO: 02, SEQ ID NO: 03, SEQ ID NO: 04, SEQ ID NO: 05, SEQ ID NO: 06, and SEQ ID NO: 07. The expression vector can also include a target nucleotide sequence under control of the promoter, where the target nucleotide sequence encodes an exogenous target protein. In another aspect, the promoter nucleotide sequence can have a sequence selected from SEQ ID NO: 01, SEQ ID NO: 02, SEQ ID NO: 03, SEQ ID NO: 04, SEQ ID NO: 05, SEQ ID NO: 06, SEQ ID NO: 07, and compliments thereof.

The scope of the present disclosure includes any expression vector or other expression vehicle capable of receiving a promoter nucleotide sequence and a target nucleotide sequence, and that can subsequently express an exogenous target protein therefrom. Non-limiting examples of such expression vectors can include various plasmid, virus, or vector DNAs that can be introduced into cells to drive expression of encoded proteins from a eukaryotic promoter, for example pcDNA™3.1/myc-His(−)A-based plasmids.

The present disclosure additionally provides methods of manipulating cellular rescue following siRNA silencing. In one aspect, for example, a method of regulating rescue of a cellular phenotype induced by siRNA transfection in a cell can include delivering siRNA into a population of cells, the siRNA being complementary to mRNA that encodes an endogenous target protein, and verifying the at least substantial absence of the endogenous target protein from the cells. The method can additionally include delivering at least one expression vector into the population of cells and measuring expression of the exogenous target protein in the population of cells. In some aspects, the expression vector can include a non-natural modified CMV promoter having a promoter nucleotide sequence that is at least 80% homologous to a sequence selected from SEQ ID NO: 01, SEQ ID NO: 02, SEQ ID NO: 03, SEQ ID NO: 04, SEQ ID NO: 05, SEQ ID NO: 06, and SEQ ID NO: 07. The expression vector can also include a target nucleotide sequence under control of the promoter, where the target nucleotide sequence encodes an exogenous target protein. In another aspect, the promoter nucleotide sequence can have a sequence selected from SEQ ID NO: 01, SEQ ID NO: 02, SEQ ID NO: 03, SEQ ID NO: 04, SEQ ID NO: 05, SEQ ID NO: 06, SEQ ID NO: 07, and compliments thereof. In some cases, measuring expression of the exogenous target protein includes measuring a rescued phenotype of at least a portion of the population of cells. In other cases, the expression of the exogenous target protein can be measured directly through a variety of biotechnological methods.

In another aspect, delivering the at least one expression vector into the population of cells can further include delivering at least two expression vectors having distinct promoters independently into the population of cells and the expression of the exogenous target protein in the population of cells can be measured to determine which of the at least two expression vectors provides an appropriate expression level of the exogenous target protein. In yet another aspect, wherein delivering the at least two expression vectors independently into the population of cells further includes delivering the at least two expression vectors independently into the population of cells such that each cell receives only a single expression vector. Additionally, in further aspects seven expression vectors independently including the nucleotide sequences SEQ ID NO: 01, SEQ ID NO: 02, SEQ ID NO: 03, SEQ ID NO: 04, SEQ ID NO: 05, SEQ ID NO: 06, and SEQ ID NO: 07 can be delivered into the population of cells.

The present disclosure additionally provides various non-natural cell populations. In one aspect, for example, a non-natural population of cells can include siRNA blocking expression of an endogenous target protein, an expression vector including a non-natural modified CMV promoter having a promoter nucleotide sequence that is at least 80% homologous to a sequence selected from SEQ ID NO: 01, SEQ ID NO: 02, SEQ ID NO: 03, SEQ ID NO: 04, SEQ ID NO: 05, SEQ ID NO: 06, and SEQ ID NO: 07, and a nucleotide sequence under control of the promoter, where the nucleotide sequence encodes an exogenous target protein. In another aspect, the promoter nucleotide sequence can have a sequence selected from SEQ ID NO: 01, SEQ ID NO: 02, SEQ ID NO: 03, SEQ ID NO: 04, SEQ ID NO: 05, SEQ ID NO: 06, SEQ ID NO: 07, and compliments thereof.

There has thus been outlined, rather broadly, various features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

DETAILED DESCRIPTION OF THE INVENTION

Figure 1:
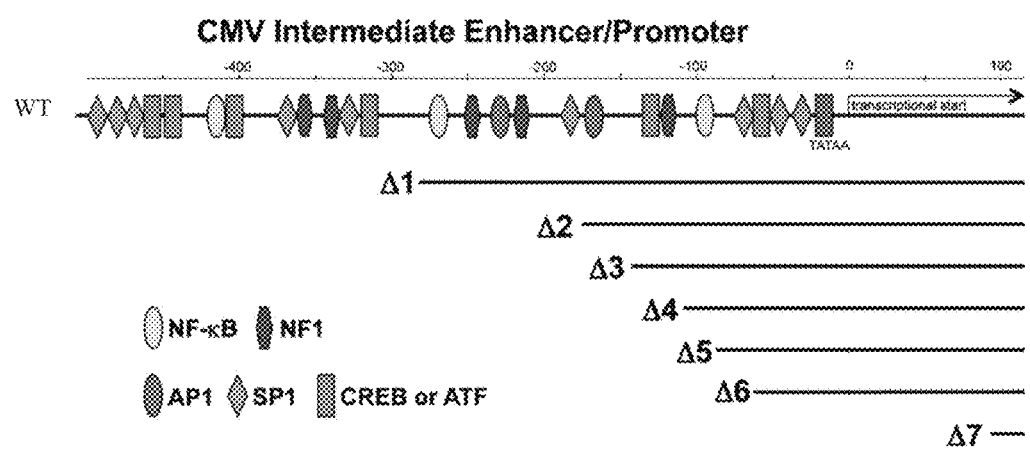
FIG. 1 provides a schematic view of a CMV intermediate enhancer/promoter including a series of modified promoters in accordance with one embodiment of the present disclosure.

In describing and claiming the present invention, the following terminology will be used in accordance with the definitions set forth below.

The singular forms "a," "an," and, "the" include plural referents unless the context clearly dictates otherwise. Thus, for example, reference to "a nucleotide" includes reference to one or more of such nucleotides, and reference to "the oligonucleotide" includes reference to one or more of such oligonucleotides.

As used herein, the term "endogenous" as it relates to a target protein can refer to any protein that is expressed by a cell from the cellular genome. Such "endogenous" target proteins can thus include any protein expressed from genetic material normally found within a cell, as well as, for the purposes of this disclosure, from genetic material that has been inserted into the cellular genome. Additionally, "endogenous" would not include target proteins generated via an expression vector or other expression vehicle that is distinct from the cellular genome.

As used herein, the term "exogenous" as it relates to a target protein can refer to any protein that is not expressed by a cell from the cellular genome. Such "exogenous" target proteins can thus exclude any protein expressed from genetic material normally found within a cell, as well as, for the purposes of the present disclosure, from genetic material that has been inserted into the cellular genome. Additionally, "exogenous" would include target proteins generated via an expression vector or other expression vehicle that is distinct from the cellular genome.

As used herein, the term "non-natural" refers to a nucleotide sequence, protein sequence, cell, cell population, etc., that has been deliberately modified and thus does not occur in nature. For example, a CMV promoter that has been deliberately modified from the wild type sequence would be defined as a "non-natural" promoter. It is additionally noted that a "non-natural" cell is defined as a cell that, among other things, is expressing an exogenous target protein.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

The present disclosure addresses, among other things, techniques for affecting exogenous protein expression levels. In many cases, expression vectors can express a protein of interest at a level that is not optimal for the expression purpose, whether it be overexpression or under expression. In some cases, for example, overexpression of the protein at high levels can be toxic to a cell. In other cases, overexpression of a protein can obscure associated protein pathways, and can alter phenotypic response.

It is now thus disclosed that the strength of a promoter can be altered in order to affect expression levels of an associated protein. More specifically, deleting specific portions of a promoter can reduce protein expression levels. In a similar manner, serial deletions can be performed on the promoter to generate a series of non-natural promoters that express proteins at different expression levels.

Such promoters can be used for a variety of purposes, and it should be understood that any such purpose for which such a modified promoter would be useful is considered to be within the present scope. In one aspect, however, modified promoters can be used to down regulate exogenous protein expression in situations where high levels of such protein is toxic for cells. In another aspect, modified promoters can be used in situations where proper processing of the exogenously expressed protein is facilitated, and in some cases can only occur, when the protein is expressed at an optimal level. One example may include situations where high levels of protein expression negatively affect optimal folding. This may include the situation, among others, where too high a level of expression level exceeds the capability of the chaperone machinery. Modified promoters can also be useful where expression levels affect post-translational modifications, as may be the case, among others, where too high expression level can exceed the capability of modifying enzymes. In another example, modified promoters can be useful where expression levels affect subcellular localization, as may be the case, among others, where too high expression level can exceed the capability of transport or retention machinery. In other aspects, modified promoters can be used in situations where can be beneficial to control the amount of exogenous protein expression in the cell to promote stoichiometric complex formation and/or protein-protein interactions. In yet other aspects, modified promoters can be utilized to investigate protein function by matching exogenous expression levels to endogenous expression levels, in some cases without eliminating the endogenous protein. Furthermore, and yet other aspects such modified promoters can be utilized for drug target validation studies in drug discovery genetic rescue, genetic complementation, and the like).

While a variety of promoters can be modified and subsequently utilized and are thus considered to be within the present scope, in one specific aspect the human cytomegalovirus (CMV) inteiniediate early enhancer/promoter can be beneficial due, in part, to its robust protein expression. The present non-natural CMV promoters allow more precise control of exogenous protein expression levels when utilized with an appropriate expression vector. Serial deletions of these modified CMV promoters have nested deletions that successively eliminate transcription factor binding sites (see FIG. 1 and Table 1).

TABLE 1

| Plasmid Name | Internal Number | Backbone | Insert | Cloning Sites |
|---|---|---|---|---|
| pCMV(WT) | WISP12-91 | | | |
| pCMV(Δ1) | WISP12-92 | | | |
| pCMV(Δ2) | WISP12-93 | | | |
| pCMV(Δ3) | WISP12-94 | | | |
| pCMV(Δ4) | WISP12-95 | | | |
| pCMV(Δ5) | WISP12-96 | | | |
| pCMV(Δ6) | WISP12-97 | | | |
| pCMV(Δ7) | WISP12-98 | | | |
| pCMV(WT)-CHMP2A | WISP12-89 | pCMV(WT) | CHMP2A sichmp2A395 resistant | KpnI, XhoI |
| pCMV(Δ1)-CHMP2A | WISP12-99 | pCMV(Δ1) | CHMP2A sichmp2A395 resistant | KpnI, XhoI |
| pCMV(Δ2)-CHMP2A | WISP12-100 | pCMV(Δ2) | CHMP2A sichmp2A395 resistant | KpnI, XhoI |
| pCMV(Δ3)-CHMP2A | WISP12-101 | pCMV(Δ3) | CHMP2A sichmp2A395 resistant | KpnI, XhoI |
| pCMV(Δ4)-CHMP2A | WISP12-102 | pCMV(Δ4) | CHMP2A sichmp2A395 resistant | KpnI, XhoI |
| pCMV(Δ5)-CHMP2A | WISP12-103 | pCMV(Δ5) | CHMP2A sichmp2A395 resistant | KpnI, XhoI |
| pCMV(Δ6)-CHMP2A | WISP12-104 | pCMV(Δ6) | CHMP2A sichmp2A395 resistant | KpnI, XhoI |
| pCMV(Δ7)-CHMP2A | WISP12-105 | pCMV(Δ7) | CHMP2A sichmp2A395 resistant | KpnI, XhoI |
| pCMV(WT)-YFP | WISP12-106 | pCMV(WT) | YFP | KpnI, XhoI |
| pCMV(Δ1)-YFP | WISP12-107 | pCMV(Δ1) | YFP | KpnI, XhoI |
| pCMV(Δ2)-YFP | WISP12-108 | pCMV(Δ2) | YFP | KpnI, XhoI |
| pCMV(Δ3)-YFP | WISP12-109 | pCMV(Δ3) | YFP | KpnI, XhoI |
| pCMV(Δ4)-YFP | WISP12-110 | pCMV(Δ4) | YFP | KpnI, XhoI |
| pCMV(Δ5)-YFP | WISP12-111 | pCMV(Δ5) | YFP | KpnI, XhoI |
| pCMV(Δ6)-YFP | WISP12-112 | pCMV(Δ6) | YFP | KpnI, XhoI |
| pCMV(Δ7)-YFP | WISP12-113 | pCMV(Δ7) | YFP | KpnI, XhoI |

FIG. 1 shows examples of modified CMV promoter constructs that can be used for attenuated gene expression. The human CMV promoter structure is shown with the transcription start site at the +1 position and (putative) upstream binding sites for different transcription factors. Promoter deletion positions are shown beneath the wild type (WT) promoter. Transcription factor binding elements were identified using the TESS analysis tool, with a consensus sequence cutoff of >12.0. Promoter deletions were introduced by cloning PCR fragments (MluI-XbaI sites) with the designated deletions into a pcDNA 3.1/myc-His(−)A expression vector (Life Technologies) that carried a custom multicloning site between the XbaI and AflIII sites. Constructs are described in Table 1. Sequences for each of the CMV promoters described include CMVΔ1 (SEQ ID NO: 01), CMVΔ2 (SEQ ID NO: 02), CMVΔ3 (SEQ ID NO: 03), CMVΔ4 (SEQ ID NO: 04), CMVΔ5 (SEQ ID NO: 05), CMVΔ6 (SEQ ID NO: 06), CMVΔ7 (SEQ ID NO: 07), and CMVWT (SEQ ID NO: 08). The promoter deletions in constructs CMVΔ1-4 and CMVΔ6 were initially designed to remove each of the consensus repeats sequentially and the deletion in CMVΔ7 was designed to remove the CMV promoter entirely (negative control). Preliminary experiments show that the deletion between CMVΔ4 and CMVΔ6 causes a large drop in protein expression; the intermediate CMVΔ5 construct was therefore designed to remove the intervening NF-κB binding site while retaining the intervening SP1 binding site.

As such, in one aspect a non-natural modified CMV promoter is provided having a promoter nucleotide sequence that is at least 80% homologous to a sequence selected SEQ ID NO: 01, SEQ ID NO: 02, SEQ ID NO: 03, SEQ ID NO: 04, SEQ ID NO: 05, SEQ ID NO: 06, SEQ ID NO: 07, and compliments thereof. In another aspect, the promoter can having a promoter nucleotide sequence selected from SEQ ID NO: 01, SEQ ID NO: 02, SEQ ID NO: 03, SEQ ID NO: 04, SEQ ID NO: 05, SEQ ID NO: 06, SEQ ID NO: 07, or compliments thereof. In yet another aspect, the promoter can have the promoter nucleotide sequence of SEQ ID NO: 01 or a compliment thereof. In yet another aspect, the promoter can have the promoter nucleotide sequence of SEQ ID NO: 02 or a compliment thereof in yet another aspect, the promoter can have the promoter nucleotide sequence of SEQ ID NO: 03 or a compliment thereof. In yet another aspect, the promoter can have the promoter nucleotide sequence of SEQ ID NO: 04 or a compliment thereof. In yet another aspect, the promoter can have the promoter nucleotide sequence of SEQ ID NO: 05 or a compliment thereof. In yet another aspect, the promoter can have the promoter nucleotide sequence of SEQ ID NO: 06 or a compliment thereof. In yet another aspect, the promoter can have the promoter nucleotide sequence of SEQ ID NO: 07 or a compliment thereof.

In yet another aspect, an expression vector is provided including a non-natural modified CMV promoter having a promoter nucleotide sequence that is at least 80% homologous to a sequence selected from SEQ ID NO: 01, SEQ ID NO: 02, SEQ ID NO: 03, SEQ ID NO: 04, SEQ ID NO: 05, SEQ ID NO: 06, or SEQ ID NO: 07. The expression vector can also include a target nucleotide sequence under control of the promoter, where the target nucleotide sequence encodes an exogenous target protein. In another aspect, the promoter nucleotide sequence can have a promoter sequence selected from SEQ ID NO: 01, SEQ ID NO: 02, SEQ ID NO: 03, SEQ ID NO: 04, SEQ ID NO: 05, SEQ ID NO: 06, SEQ ID NO: 07, and compliments thereof. In yet another aspect, the promoter can have the promoter nucleotide sequence of SEQ ID NO: 01. In yet another aspect, the promoter can have the promoter nucleotide sequence of SEQ ID NO: 02. In yet another aspect, the promoter can have the promoter nucleotide sequence of SEQ ID NO: 03. In yet another aspect, the promoter can have the promoter nucleotide sequence of SEQ ID NO: 04. In yet another aspect, the promoter can have the promoter nucleotide sequence of SEQ ID NO: 05. In yet another aspect, the promoter can have the promoter nucleotide sequence of SEQ ID NO: 06. In yet another aspect, the promoter can have the promoter nucleotide sequence of SEQ ID NO: 07.

Furthermore, the expression vector can include any expression vector or other expression vehicle capable of receiving a promoter nucleotide sequence and a target nucleotide sequence, and that can subsequently express an exogenous target protein therefrom. Non-limiting examples of such expression vectors can include various plasmid, virus, or vector DNAs that can be introduced into cells to drive expression of encoded proteins from a eukaryotic promoter, for example pcDNA™3.1/myc-His(−)A-based plasmids.

In one specific aspect, the present modified promoters can allow tunable expression of siRNA-resistant constructs. Such modified promoters can be utilized in mammalian and/or non-mammalian expression vectors and systems. Furthermore, it is demonstrated that these promoters are beneficial in rescuing a target protein or a cellular process, such as, for example, HIV-1 budding from cells that lacked endogenous CHMP2 proteins. The present system can additionally be successfully performed in a variety of other experimental situations such as, in addition to those examples described elsewhere within, to achieve high-level rescue of retrovirus budding from cells depleted of endogenous ALIX and CHMP4 proteins. In one aspect, a vector containing an optimal modified CMV promoter can be determined empirically for each new system because a choice can be made based on differences in endogenous protein levels, protein expression efficiencies, and the degree to which the specific pathway and cell type can tolerate protein overexpression. The present system can be particularly useful in cases where levels of the rescue protein benefit from being tightly controlled and where the creation of stable cell lines is overly time consuming or problematic. The present expression vectors can also be useful in other applications where it is desirable to attenuate protein expression while maintaining high transfection levels.

The present disclosure additionally provides methods of manipulating cellular rescue following siRNA silencing. In one aspect, for example, a method of regulating rescue of a cellular phenotype induced by siRNA transfection in a cell can include delivering siRNA into a population of cells, the SiRNA being complementary to mRNA that encodes an endogenous target protein, and verifying at least the substantial absence of the endogenous target protein from the cells. The method can additionally include delivering at least one expression vector into the cells, where the at least one expression vector has a target nucleotide sequence under control of a modified CMV promoter, where the target nucleotide sequence encodes an exogenous target protein. The method can further include measuring expression of the exogenous target protein in the population of cells. Measuring expression can be by any known technique, including phenotypic measurement as well as direct assaying of the exogenous protein.

In another aspect, a method of regulating rescue of a cellular phenotype induced by siRNA transfection in a cell can include delivering siRNA into a population of cells, the SiRNA being complementary to mRNA that encodes an endogenous target protein, and verifying at least the substantial absence of the endogenous target protein from the cells. The method can further include delivering at least two expression vectors independently into the population of cells, wherein each expression vector includes a distinct non-natural modified CMV promoter having a nucleotide sequence selected from SEQ ID NO: 01, SEQ ID NO: 02, SEQ ID NO: 03, SEQ ID NO: 04, SEQ ID NO: 05, SEQ ID NO: 06, or SEQ ID NO: 07, and a nucleotide sequence encoding an exogenous target protein and under control of the promoter, wherein each promoter expresses the exogenous target protein at a different expression level. The method can further include measuring expression of the exogenous target protein in the population of cells to determine which of the at least two expression vectors provides an appropriate expression level of the exogenous target protein. In some aspects the expression vectors can be delivered such that on average each cell receives only a single expression vector. In another aspect, delivering at least two expression vectors can include seven expression vectors independently including the nucleotide sequences SEQ ID NO: 01, SEQ ID NO: 02, SEQ ID NO: 03, SEQ ID NO: 04, SEQ ID NO: 05, SEQ ID NO: 06, and SEQ ID NO: 07 delivered into the population of cells.

Additionally, in some aspects the present disclosure provides non-natural cells and populations of cells. In one aspect such a cell can include siRNA blocking expression of an endogenous target protein and an expression vector including a non-natural modified CMV promoter having a promoter nucleotide sequence that is at least 80% homologous to a sequence selected from the group consisting of SEQ ID NO: 01, SEQ ID NO: 02, SEQ ID NO: 03, SEQ ID NO: 04, SEQ ID NO: 05, SEQ ID NO: 06, and SEQ ID NO: 07. The expression vector can also include a nucleotide sequence under control of the promoter, where the nucleotide sequence encodes an exogenous target protein. In yet another aspect, the promoter nucleotide sequence can have a sequence selected from SEQ ID NO: 01, SEQ ID NO: 02, SEQ ID NO: 03, SEQ ID NO: 04, SEQ ID NO: 05, SEQ ID NO: 06, SEQ ID NO: 07, and compliments thereof.

Although any suitable expression vector is contemplated, in one aspect the deletions can be made in the context of the mammalian expression vector pcDNA 3.1/myc-His(–)A, that contain a custom-designed multiple cloning site (MCS) cassette. These vectors allow optimized expression of siRNA-resistant constructs while maintaining the high transfection efficiencies necessary for potent phenotypic rescue.

Furthermore, it is noted that any target protein or protein system that is compatible with the present techniques can be utilized in conjunction with such expression vectors. As such, the present scope should not be limited by the following protein and protein system descriptions. That being said, HIV-1 and many other enveloped viruses recruit the cellular endosomal sorting complexes required for transport (ESCRT) pathway to facilitate the final membrane fission step of virus budding. As is true for many other cellular pathways, siRNA depletion/rescue experiments have contributed to the understanding of the role of the ESCRT pathway in HIV-1 budding. The inventors have discovered, however, that it can be difficult to rescue virus budding to wild type levels following siRNA depletion because many ESCRT proteins, particularly those of the ESCRT-III family, can potently inhibit HIV-1 budding when overexpressed at elevated levels. The ESCRT-III/HIV-1 system therefore represents a non-limiting test system for examining the utility of the present attenuated CMV expression vectors.

Figure 2A:
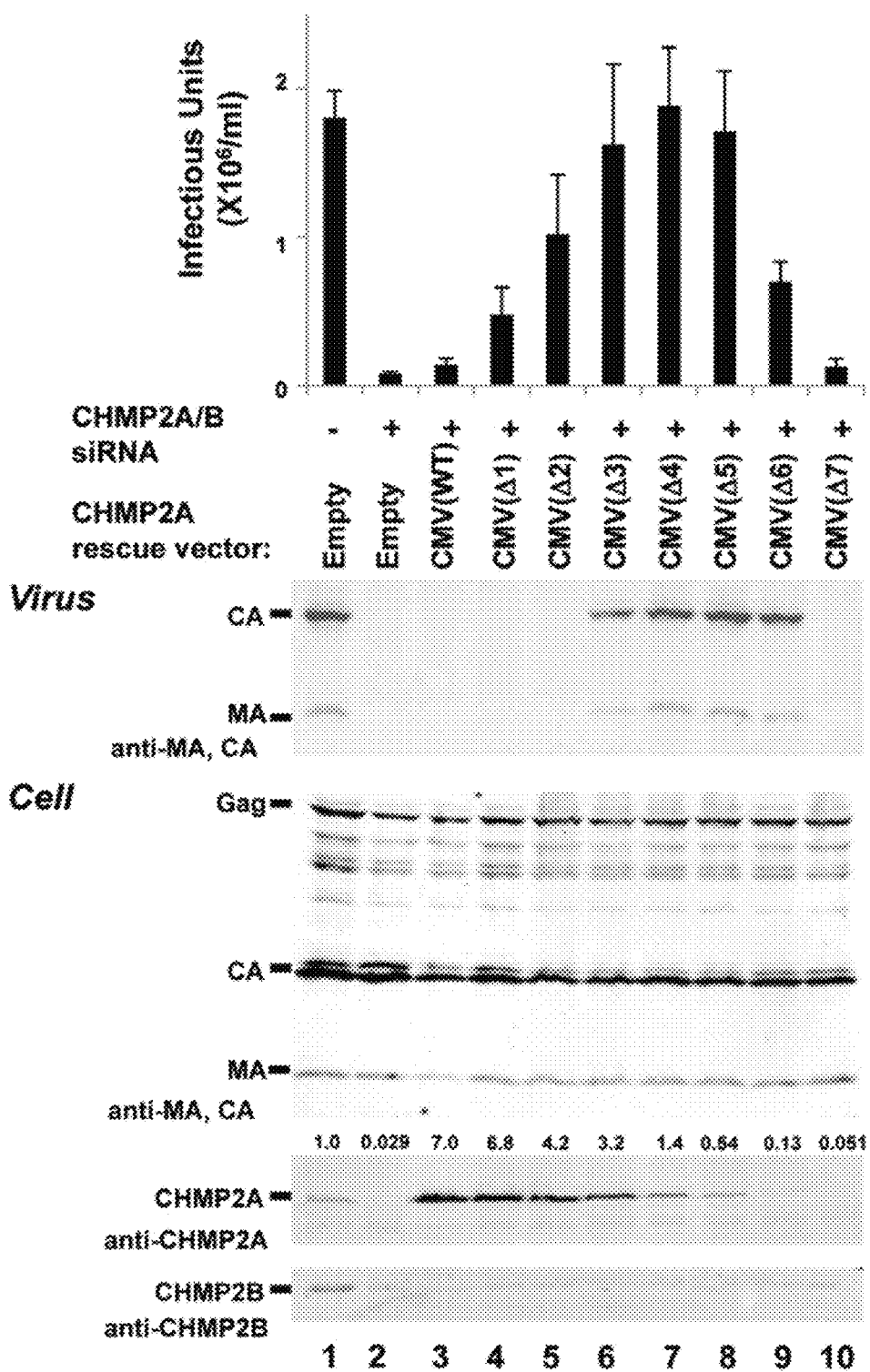
FIG. 2A provides data showing rescue of HIV-1 budding from 293T cells in accordance with one embodiment of the present disclosure.

HIV-1 budding from cultured 29317 cells can be potently inhibited by co-depletion of both members of the human CHMP2 family of ESCRT-III proteins (denoted CHMP2A and CHMP2B). As one example, FIG. 2A shows rescue of HIV-1 budding from 293T cells that lack endogenous CHMP2 proteins by expression of human CHMP2A from attenuated CMV expression vectors. Differential rescue of HIV-1 budding by CHMP2A proteins expressed from the ensemble of different pCMV-CHMP2A expression vectors is demonstrated. HIV-1 vector infectivity titers (top panel) and Western blots showing protein levels in culture supernatants (panel 2) or 293T cells (Cell, panels 3-5) co-transfected with a proviral HIV-1 vector (500 ng of pCMV-dR8.2, 500 ng pLox-GFP, 250 ng pMD-G) (all lanes), either 20 nM control siRNA duplex (CGUACGCGGAAUAC-UUCGAtt (SEQ ID NO: 09), where "tt" represents two overhanging deoxyribothymidines, lanes 1) or 10 nM each of siRNA duplexes against CHMP2A and CHMP2B (AG-GCAGAGAUCAUGGAUAUtt (SEQ ID NO: 10) and GGAACAGAAUCGAGAGUUAtt (SEQ ID NO: 11), lanes 2-10), and 500 ng of either an empty vector control (lane 2) or the designated pCMV-CHMP2A vector expressing an siRNA-resistant CHMP2A construct (lanes 3-10). Integrated. CHMP2A band intensities, normalized to the endogenous CHMP2A level, are provided over each lane in panel 4. 2931 cells (2×105 cells/well, 6-well plates, 2 mL volume) were seeded at t=0, transfected with siRNA (20 nM final total concentration, 7.5 µl Lipofectamine RNAiMAX; Life Technologies, Carlsbad, Calif., USA) at t=24h, and co-transfected with siRNA, the designated pCMV-CHMP2A vector (500 ng), and the HIV-1 vector (20 nM final total siRNA concentration, 500 ng pCMV-dR8.2, 500 ng pLox-GFP, 250 ng pMD-G, 10 µl Lipofectamine 2000; Life Technologies) at t=48h. The following silent mutations were introduced into the CHMP2A cDNA coding sequence to make the CHMP2A mRNA siRNA resistant: AGGCAGA-GATCATGGATAT (SEQ NO: 12) to AaGCtGAaATtATG-GATAT (SEQ ID NO: 13) (nucleotides 395-413). Cells and supernatant were collected and analyzed at t=96h. Released virions were pelleted through a 20% sucrose cushion at 15,000×g and viral Gag-derived proteins were detected by Western blotting using the inventor's rabbit anti-HIV-1 CA (U1415, 1:2000) and MA (U1556, 1:1000) antisera. Cells were lysed with buffer (50 mM Tris-HCl pH 7.4, 150 mM NaCl, 1% Triton-X100, and PMSF) for Western blotting of intracellular proteins. Anti-CHMP2A and CHMP2B were detected with U1589 (the inventor's antibody) and Ab33174 (Abcam, Cambridge, Mass., USA). Secondary antibodies were anti-mouse IgG or anti-rabbit IgG polyclonal conjugated to IRdye700 or IRdye800 (1:10000, Rockland Immunochemicals Inc., Gilbertsville, Pa., USA). Western blots were visualized using an Odyssey scanner (Li-Cor Biosciences, Lincoln, NB, USA). For titer measurements, 2931 cells were infected with viral supernatants and GFP-positive cells were quantified by flow cytometry (FL1 channel, FACScan, BD Biosciences, San Jose, Calif., USA). Values show the average of three independent repetitions with standard errors.

Hence, vector titers can be dramatically reduced 48 hours after co-transfection of a proviral vector together with siRNAs that target both CHMP2 proteins (FIG. 2A, 24±5-fold reduction, compare lanes 1 and 2). CHMP2 depletion can also block virus release into the culture supernatant, as measured by immunoblotting for the virion-associated structural proteins, MA and CA (FIG. 2A, panel 2, compare lanes 1 and 2). Western blots of the 293T producing cells demonstrate that both CHMP2A and CHMP2B are depleted efficiently (FIG. 2A, panels 4 and 5, compare lanes 1 and 2) and that cellular levels of the structural HIV-1 Gag protein and its MA and CA cleavage products are not altered significantly by CHMP2 protein depletion (FIG. 2A, panel 3, compare lanes 1 and 2).

To test for rescue of virus budding, 500 ng of each of the different siRNA-resistant pCMV-CHMP2A expression vectors were co-transfected together with the siRNA and proviral HIV-1 (FIG. 2A). CHMP2A expression levels were highest for the construct that carried the wild type CMV promoter (denoted pCMV(WT)-CHMP2A) and decreased successively over two orders of magnitude as larger and larger promoter deletions were introduced (denoted pCMV(Δ1)-CHMP2A to pCMV(Δ7)-CHMP2A, (FIG. 2A, panel 4, compare lanes 3-10)). In contrast, the rescue of virus budding was biphasic: virion release and infectivity were low when CHMP2A levels were highest, increased when CHMP2A was expressed at intermediate levels, and then decreased again at the lowest CHMP2A expression levels (FIG. 2A, panels 1 and 2, compare lanes 3-10). Levels of virion release and infectivity generally correlated well, but maximal infectivity occurred at slightly higher CHMP2A levels, perhaps because rapid virus release kinetics contribute more to viral infectivity than to total virion release as measured in the end point release assay. The pCMV(Δ4)-CHMP2A and pCMV(Δ5)-CHMP2A constructs expressed CHMP2A at levels that most closely approximated the normal level of the endogenous protein (FIG. 2A, panel 4, compare lanes 7 and 8 to lane 1). These two CHMP2A expression constructs also rescued virus release and infectivity best (FIG. 2A, panels 1 and 2). Importantly, the pCMV(Δ4)-CHMP2A construct rescued viral titers very efficiently, to 102=r=12% of untreated control levels. Without intending to be bound by any scientific theory, these data imply that: (i) CHMP2A alone can fully rescue HIV-1 budding, even in the absence of CHMP2B; (ii) CHMP2A functions best when expressed at near-native levels; and (iii) the attenuated pCMV(Δ4)-CHMP2A and pCMV(Δ5)-CHMP2A constructs can express near-native levels of CHMP2A under conditions where transfection efficiencies apparently remain high.

Figure 2B:
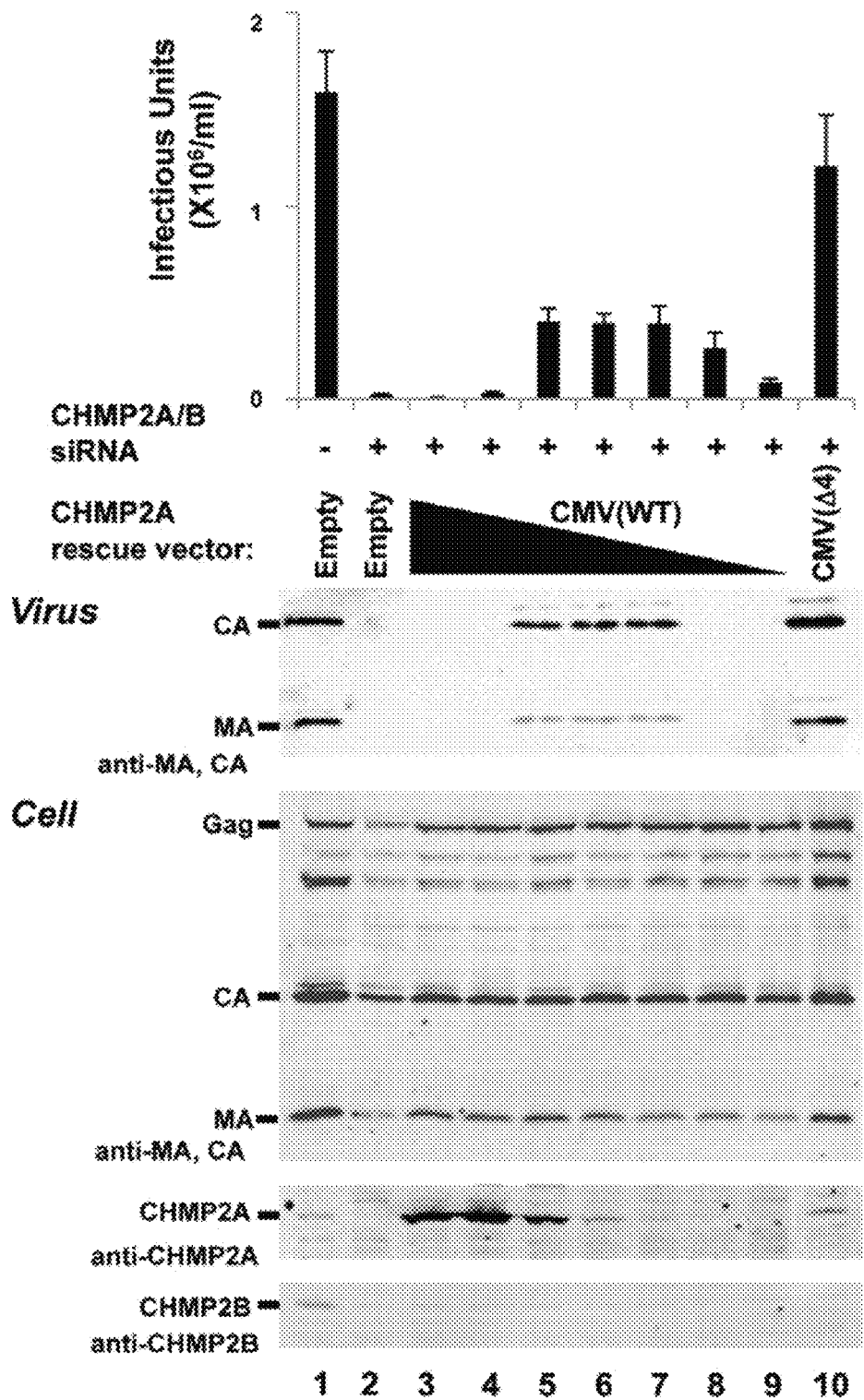
FIG. 2B provides data showing rescue of HIV-1 budding from 293T cells in accordance with one embodiment of the present disclosure.

It was next tested whether HIV-1 budding could be rescued to comparable levels simply by varying the quantity of pCMV(WT)-CHMP2A used in the transfection reaction. 3-fold dilutions over a range of 500-0.69 ng of pCMV(WT)-CHMP2A were tested for rescue of HIV-1 budding from cells that lacked endogenous CHMP2 proteins. FIG. 2B shows rescue of HIV-1 budding by CHMP2A proteins expressed from different quantities of the wild type CMV expression vector, pCMV(WT)-CHMP2A. FIG. 2B and the experiments are substantially similar to FIG. 2A, with the exception that the following quantities of the siRNA-resistant CHMP2A rescue construct pCMV(WT)-CHMP2A were transfected: 500 ng (lane 3), 170 ng (lane 4), 56 ng (lane 5), 19 ng (lane 6), 6.2 ng (lane 7), 2.1 ng (lane 8), and 0.69 ng (lane 9). In the experiments shown in lanes 4-9, total expression vector levels were adjusted to 500 ng with pCMV(WT) empty vector. The sample shown in lane 10 was transfected with 500 rig of the pCMV(Δ4)-CHMP2A expression vector (positive control).

As such, CHMP2A expression levels correlated well with the quantity of pCMV(WT)-CHMP2A vector used (FIG. 2B, panel 4, lanes 3-9), and CHMP2A levels most closely approximated normal endogenous protein levels when 56 and 19 ng of pCMV(WT)-CHMP2A were used (compare lane 1 to lanes 6 and 7). Rescue of HIV-1 budding again followed a biphasic curve, with optimal rescue observed when CHMP2A was expressed at intermediate levels (170-19 ng pCMV(WT)-CHMP2A, lanes 5-7). In this case, however, HIV-1 titers never exceeded 26% of control levels, even when the bulk levels of exogenous CHMP2A approximated endogenous control levels (FIG. 2B, panel 1, compare lane 1 to lanes 6 and 7). In a parallel control experiment, HIV-1 release was again rescued to nearly wild type levels upon co-transfection of 500 ng of the pCMV(Δ4)-CHMP2A construct (lane 10). It is therefore concluded that although optimizing pCMV(WT)-CHMP2A vector levels improved HIV-1 budding, overall rescue levels were never as high as could be achieved with the attenuated pCMV(Δ4)-CHMP2 expression construct.

Figure 3A:
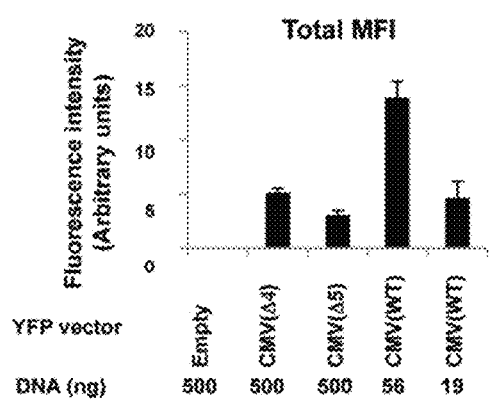
FIG. 3A provides data showing the comparison of transfection efficiencies and protein expression levels for different CMV promoters in accordance with one embodiment of the present disclosure.
Figure 3B:
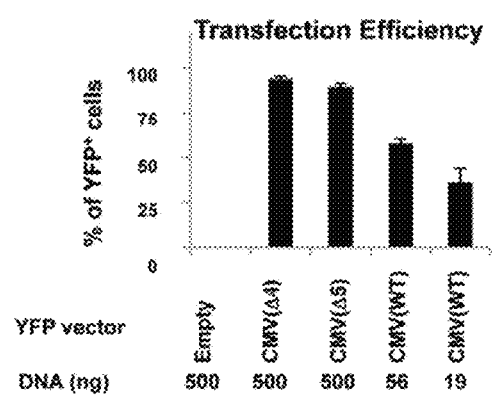
FIG. 3B provides data showing the comparison of transfection efficiencies and protein expression levels for different CMV promoters in accordance with one embodiment of the present disclosure.
Figure 3C:
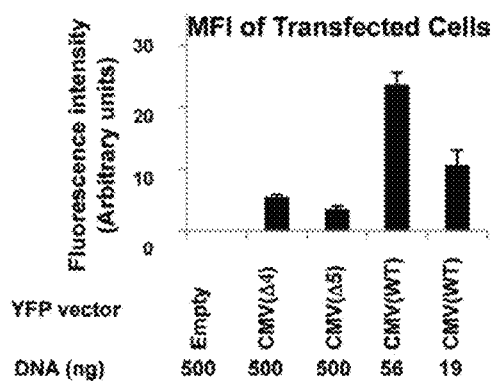
FIG. 3C provides data showing the comparison of transfection efficiencies and protein expression levels for different CMV promoters in accordance with one embodiment of the present disclosure.

It was hypothesized that the pCMV(Δ4)-CHMP2A and pCMV(Δ5)-CHMP2A vectors worked well in the rescue experiment because they could be used at concentrations that coupled high transfection efficiencies with restricted protein expression. To test this idea, the inventors created pCMV(WT)-YFP, pCMV(Δ4)-YFP and pCMV(Δ5)-YFP expression vectors and used YFP fluorescence as a measure of protein expression in 293T cells. This approach allowed us to use flow cytometry to quantify transfection efficiencies and relative protein expression levels at the single-cell level. Titrations were again performed to determine the quantity of pCMV(WT)-YFP required to express YFP at levels comparable to those produced by transfections with 500 ng of pCMV(Δ4)-YFP or pCMV(Δ5)-YFP. This was achieved with 19 ng of pCMV(WT)-YFP, in reasonable agreement with the analogous CHMP2A titration experiments (FIG. 3A, compare total mean fluorescence levels for 500 ng of pCMV(Δ4)-YFP or pCMV(Δ5)-YFP DNA with 19 ng of pCMV(WT)-YFP). FIG. 3 in general shows a comparison of transfection efficiencies and protein expression levels for the pCMV(WT)-YFP, pCMV(Δ4)-YFP, and pCMV(Δ5)-YFP vectors. The YFP expression vectors were created by PCR amplification of the yfp gene and subcloned into the KpnI/XhoI sites of the custom multiple cloning site of the pcDNA 3.1/myc-His(-)A expression vector. 293T cells were seeded (t=0, 2×105 cells/well, 6-well plates) and transfected (t=24h) with the designated pCMV-YFP constructs (adjusted to 500 ng total DNA with pCMV(WT) empty vector where necessary), 10 μl Lipofectamine 2000). At t=72h, cells were trypsinized and analyzed by flow cytometry. YFP-positive cells were scored using a control-transfected sample to set the negative background level (BD CellQuest Pro software). YFP intensity was determined after subtracting control-transfected samples (FL1). Values here and in panels B and C show the average of five independent repetitions with standard errors. As has been described, FIG. 3A shows the total mean fluorescence intensity of YFP (MFI, in arbitrary units) for all cells in each of the cultures following transfection with 500 ng empty pCMV(WT)(negative control, lane 1), 500 ng pCMV(Δ4)-YFP (lane 2), 500 ng pCMV(Δ5)-YFP (lane 3), 56 ng pCMV(WT)-YFP (lane 4), or 19 ng pCMV(WT)-YFP (lane 5). FIG. 3B shows percentages of cells with detectable YFP fluorescence in each of the cultures. FIG. 3C shows mean YFP fluorescence intensity (arbitrary units) for the subsets of cells that were transfected (as judged by detectable YFP expression) in each of the cultures.

As shown in FIG. 3B, overall transfection efficiencies under these three conditions were: 94±1% for 500 ng of pCMV(Δ4)-YFP, 90±2% for 500 ng of pCMV(Δ5)-YFP DNA and 36±8% for 19 ng pCMV(WT)-YFP (compare lanes 2, 3 and 5). Thus, overall transfection efficiencies dropped off significantly when the quantity of vector was reduced from 500 to 19 ng. It was also quantified that the mean fluorescence intensity (MFI) in the subsets of cells that were actually transfected in each reaction (i.e., now excluding cells in which YFP expression was undetectable). As shown in FIG. 3C, transfected cells in the 19 ng pCMV(WT)-YFP reaction had a MFI of 11±2, whereas transfected cells in the 500 ng pCMV(Δ4)-YFP and pCMV(Δ5)-YFP reactions had MFI of 5.4±0.4 and 3.4±0.6. These data demonstrate that although bulk YFP expression levels were comparable for the three conditions, this was achieved in different ways: the pCMV(Δ4)-YFP and pCMV(Δ5)-YFP vectors supported low-level YFP expression in nearly all of the cells, whereas the pCMV(WT)-YFP vector supported higher expression levels per cell, but in fewer than half of the cells. Thus, the attenuated vectors appear to work better in rescue experiments because, unlike the wild type pCMV (WT) vector, they can be used at sufficiently high concentrations to maintain high overall transfection efficiencies, yet they express low levels of the target protein in each cell. It is possible that varying vector levels could also affect the degree of rescue.

Sequences related to the present invention include the following:

```
pCMV(Wild Type):                              (SEQ ID NO: 8)
CGCTGAGTAGTGCGCGAGCAAAATTTAAGCTACAACAAGGCAAGGCTTG

ACCGACAATTGCATGAAGAATCTGCTTAGGGTTAGGCGTTTTGCGCTGC

TTCGCGATGTAC

GGGCCAGATATACGCGTTGACATTGATTATTGACTAGTTATTAATAGTA

ATCAATTACGGGGTCATTAGTTCATAGCCCATATATGGAGTTCCGCGTT

ACATAACTTACG

GTAAATGGCCCGCCTGGCTGACCGCCCAACGACCCCCGCCCATTGACGT

CAATAATGACGTATGTTCCCATAGTAACGCCAATAGGGACTTTCCATTG

ACGTCAATGGGT

GGAGTATTTACGGTAAACTGCCCACTTGGCAGTACATCAAGTGTATCAT

ATGCCAAGTACGCCCCCTATTGACGTCAATGACGGTAAATGGCCCGCCT

GGCATTATGCCC

AGTACATGACCTTATGGGACTTTCCTACTTGGCAGTACATCTACGTATT

AGTCATCGCTATTACCATGGTGATGCGGTTTTGGCAGTACATCAATGGG

CGTGGATAGCGG

TTTGACTCACGGGGATTTCCAAGTCTCCACCCCATTGACGTCAATGGGA

GTTTGTTTTGGCACCAAAATCAACGGGACTTTCCAAAATGTCGTAACAA

CTCCGCCCCATT

GACGCAAATGGGCGGTAGGCGTGTACGGTGGGAGGTCTATATAAGCAGA

GCTCTCTGGCTAACTAGAGAACCCACTGCTTACTGGCTTATCGAAATTA

ATACGACTCACT

ATAGGGAGACCCAAGCTGGCTAGCGTTTAAACGGGCCCTCTAGAATTAT

CGATCCGGAGGTACCCGGGCGGCCGCGAGTCTTCGAATTCAAACGCGTC

TCGAGAAGCTTG

CTAGCAGATCTTTTTCCCTCTGCCAAAAATTATGGGGACATCATGAAGC

CCCTTGAGCACTTAAGTTTAAACCGCTGATCAGCCTCGACTGTGCCTTC

TAGTTGCCAGCC pCMV(Δ1):                                     (SEQ ID NO: 1)
CGCTGAGTAGTGCGCGAGCAAAATTTAAGCTACAACAAGGCAAGGCTTG

ACCGACAATTGCATGAAGAATCTGCTTAGGGTTAGGCGTTTTGCGCTGC

TTCGCGATGTAC

GGGCCAGATATACGCGTCATGACCTTATGGGACTTTCCTACTTGGCAGT

ACATCTACGTATTAGTCATCGCTATTACCATGGTGATGCGGTTTTGGCA

GTACATCAATGGGCGTGGATAGCGG

TTTGACTCACGGGGATTTCCAAGTCTCCACCCCATTGACGTCAATGGGA

GTTTGTTTTGGCACCAAAATCAACGGGACTTTCCAAAATGTCGTAACAA

CTCCGCCCCATT

GACGCAAATGGGCGGTAGGCGTGTACGGTGGGAGGTCTATATAAGCAGA

GCTCTCTGGCTAACTAGAGAACCCACTGCTTACTGGCTTATCGAAATTA

ATACGACTCACT

ATAGGGAGACCCAAGCTGGCTAGCGTTTAAACGGGCCCTCTAGAATTAT

CGATCCGGAGGTACCCGGGCGGCCGCGAGTCTTCGAATTCAAACGCGTC

TCGAGAAGCTTG

CTAGCAGATCTTTTTCCCTCTGCCAAAAATTATGGGGACATCATGAAGC

CCCTTGAGCACTTAAGTTTAAACCGCTGATCAGCCTCGACTGTGCCTTC

TAGTTGCCAGCC pCMV(Δ2):                                     (SEQ ID NO: 2)
CGCTGAGTAGTGCGCGAGCAAAATTTAAGCTACAACAAGGCAAGGCTTG

ACCGACAATTGCATGAAGAATCTGCTTAGGGTTAGGCGTTTTGCGCTGC

TTCGCGATGTAC

GGGCCAGATATACGCGTTAGCGG

TTTGACTCACGGGGATTTCCAAGTCTCCACCCCATTGACGTCAATGGGA

GTTTGTTTTGGCACCAAAATCAACGGGACTTTCCAAAATGTCGTAACAA

CTCCGCCCCATT

GACGCAAATGGGCGGTAGGCGTGTACGGTGGGAGGTCTATATAAGCAGA

GCTCTCTGGCTAACTAGAGAACCCACTGCTTACTGGCTTATCGAAATTA

ATACGACTCACT

ATAGGGAGACCCAAGCTGGCTAGCGTTTAAACGGGCCCTCTAGAATTAT

CGATCCGGAGGTACCCGGGCGGCCGCGAGTCTTCGAATTCAAACGCGTC

TCGAGAAGCTTG

CTAGCAGATCTTTTTCCCTCTGCCAAAAATTATGGGGACATCATGAAGC

CCCTTGAGCACTTAAGTTTAAACCGCTGATCAGCCTCGACTGTGCCTTC

TAGTTGCCAGCC pCMV(Δ3):                                     (SEQ ID NO: 3)
CGCTGAGTAGTGCGCGAGCAAAATTTAAGCTACAACAAGGCAAGGCTTG

ACCGACAATTGCATGAAGAATCTGCTTAGGGTTAGGCGTTTTGCGCTGC

TTCGCGATGTAC

GGGCCAGATATACGCGTACCCCATTGACGTCAATGGGAGTTTGTTTTGG

CACCAAAATCAACGGGACTTTCCAAAATGTCGTAACAACTCCGCCCCAT

T

GACGCAAATGGGCGGTAGGCGTGTACGGTGGGAGGTCTATATAAGCAGA
```

GCTCTCTGGCTAACTAGAGAACCCACTGCTTACTGGCTTATCGAAATTA

ATACGACTCACT

ATAGGGAGACCCAAGCTGGCTAGCGTTTAAACGGGCCCTCTAGAATTAT

CGATCCGGAGGTACCCGGGCGGCCGCGAGTCTTCGAATTCAAACGCGTC

TCGAGAAGCTTG

CTAGCAGATCTTTTTCCCTCTGCCAAAAATTATGGGGACATCATGAAGC

CCCTTGAGCACTTAAGTTTAAACCGCTGATCAGCCTCGACTGTGCCTTC

TAGTTGCCAGCC pCMV(Δ4): (SEQ ID NO: 4)
CGCTGAGTAGTGCGCGAGCAAAATTTAAGCTACAACAAGGCAAGGCTTG

ACCGACAATTGCATGAAGAATCTGCTTAGGGTTAGGCGTTTTGCGCTGC

TTCGCGATGTAC

GGGCCAGATATACGCGTATCAACGGGACTTTCCAAAATGTCGTAACAAC

TCCGCCCCATT

GACGCAAATGGGCGGTAGGCGTGTACGGTGGGAGGTCTATATAAGCAGA

GCTCTCTGGCTAACTAGAGAACCCACTGCTTACTGGCTTATCGAAATTA

ATACGACTCACT

ATAGGGAGACCCAAGCTGGCTAGCGTTTAAACGGGCCCTCTAGAATTAT

CGATCCGGAGGTACCCGGGCGGCCGCGAGTCTTCGAATTCAAACGCGTC

TCGAGAAGCTTG

CTAGCAGATCTTTTTCCCTCTGCCAAAAATTATGGGGACATCATGAAGC

CCCTTGAGCACTTAAGTTTAAACCGCTGATCAGCCTCGACTGTGCCTTC

TAGTTGCCAGCC pCMV(Δ5): (SEQ ID NO: 5)
CGCTGAGTAGTGCGCGAGCAAAATTTAAGCTACAACAAGGCAAGGCTTG

ACCGACAATTGCATGAAGAATCTGCTTAGGGTTAGGCGTTTTGCGCTGC

TTCGCGATGTAC

GGGCCAGATATACGCGTTGTCGTAACAACTCCGCCCCATT

GACGCAAATGGGCGGTAGGCGTGTACGGTGGGAGGTCTATATAAGCAGA

GCTCTCTGGCTAACTAGAGAACCCACTGCTTACTGGCTTATCGAAATTA

ATACGACTCACT

ATAGGGAGACCCAAGCTGGCTAGCGTTTAAACGGGCCCTCTAGAATTAT

CGATCCGGAGGTACCCGGGCGGCCGCGAGTCTTCGAATTCAAACGCGTC

TCGAGAAGCTTG

CTAGCAGATCTTTTTCCCTCTGCCAAAAATTATGGGGACATCATGAAGC

CCCTTGAGCACTTAAGTTTAAACCGCTGATCAGCCTCGACTGTGCCTTC

TAGTTGCCAGCC pCMV(Δ6): (SEQ ID NO: 6)
CGCTGAGTAGTGCGCGAGCAAAATTTAAGCTACAACAAGGCAAGGCTTG

ACCGACAATTGCATGAAGAATCTGCTTAGGGTTAGGCGTTTTGCGCTGC

TTCGCGATGTAC

GGGCCAGATATACGCGTATT

GACGCAAATGGGCGGTAGGCGTGTACGGTGGGAGGTCTATATAAGCAGA

GCTCTCTGGCTAACTAGAGAACCCACTGCTTACTGGCTTATCGAAATTA

ATACGACTCACT

ATAGGGAGACCCAAGCTGGCTAGCGTTTAAACGGGCCCTCTAGAATTAT

CGATCCGGAGGTACCCGGGCGGCCGCGAGTCTTCGAATTCAAACGCGTC

TCGAGAAGCTTG

CTAGCAGATCTTTTTCCCTCTGCCAAAAATTATGGGGACATCATGAAGC

CCCTTGAGCACTTAAGTTTAAACCGCTGATCAGCCTCGACTGTGCCTTC

TAGTTGCCAGCC pCMV(Δ7): (SEQ ID NO: 7)
CGCTGAGTAGTGCGCGAGCAAAATTTAAGCTACAACAAGGCAAGGCTTG

ACCGACAATTGCATGAAGAATCTGCTTAGGGTTAGGCGTTTTGCGCTGC

TTCGCGATGTAC

GGGCCAGATATACGCGTTCTAGAATTATCGATCCGGAGGTACCCGGGCG

GCCGCGAGTCTTCGAATTCAAACGCGTCTCGAGAAGCTTG

CTAGCAGATCTTTTTCCCTCTGCCAAAAATTATGGGGACATCATGAAGC

CCCTTGAGCACTTAAGTTTAAACCGCTGATCAGCCTCGACTGTGCCTTC

TAGTTGCCAGCC

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. An expression vector comprising:
   a non-natural modified CMV promoter having a promoter nucleotide sequence selected from the group consisting of SEQ ID NO: 01; SEQ ID NO: 02, SEQ ID NO: 03, SEQ ID NO: 04, SEQ ID NO: 05, SEQ ID NO: 06, and SEQ ID NO: 07; and
   a target nucleotide sequence under control of the promoter, the target nucleotide sequence encoding an exogenous target protein.

2. A non-natural population of cells, wherein at least a portion of the population of cells includes:
   an siRNA that is complimentary to an mRNA that encodes an endogenous target protein;
   an expression vector comprising;
     a non-natural modified CMV promoter having a promoter nucleotide sequence selected from the group consisting of SEQ ID NO: 01, SEQ ID NO: 02; SEQ ID NO: 03, SEQ ID NO: 04, SEQ ID NO: 05, SEQ ID NO: 06, and SEQ ID NO: 07; and
     a nucleotide sequence under control of the promoter, the nucleotide sequence encoding an exogenous target protein.

3. The expression vector of claim 1, wherein the promoter nucleotide sequence has the sequence of SEQ ID NO: 01.

4. The expression vector of claim 1, wherein the promoter nucleotide sequence has the sequence of SEQ ID NO: 02.

5. The expression vector of claim 1, wherein the promoter nucleotide sequence has the sequence of SEQ ID NO: 03.

6. The expression vector of claim 1, wherein the promoter nucleotide sequence has the sequence of SEQ ID NO: 04.

7. The expression vector of claim 1, wherein the promoter nucleotide sequence has the sequence of SEQ ID NO: 05.

8. The expression vector of claim 1, wherein the promoter nucleotide sequence has the sequence of SEQ ID NO: 06.

9. The expression vector of claim 1, wherein the promoter nucleotide sequence has the sequence of SEQ ID NO: 07.

10. The population of cells of claim 2, wherein the promoter nucleotide sequence has the sequence of SEQ ID NO: 01.

11. The population of cells of claim 2, wherein the promoter nucleotide sequence has the sequence of SEQ ID NO: 02.

12. The population of cells of claim 2, wherein the promoter nucleotide sequence has the sequence of SEQ ID NO: 03.

13. The population of cells of claim 2, wherein the promoter nucleotide sequence has the sequence of SEQ ID NO: 04.

14. The population of cells of claim 2, wherein the promoter nucleotide sequence has the sequence of SEQ ID NO: 05.

15. The population of cells of claim 2, wherein the promoter nucleotide sequence has the sequence of SEQ ID NO: 06.

16. The population of cells of claim 2, wherein the promoter nucleotide sequence has the sequence of SEQ ID NO: 07.

* * * * *